United States Patent
Zihajehzadeh et al.

(10) Patent No.: US 10,240,929 B2
(45) Date of Patent: Mar. 26, 2019

(54) METHODS AND SYSTEMS FOR VERTICAL TRAJECTORY DETERMINATION AND AUTOMATIC JUMP DETECTION

(71) Applicant: Intel Corporation, Santa Clara, CA (US)

(72) Inventors: Shaghayegh Zihajehzadeh, Burnaby (CA); Tien Jung Lee, Surrey (CA); Jung Wook Park, Surrey (CA); Reynald Antoine Hoskinson, Vancouver (CA); Hamid Abdollahi, Vancouver (CA)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 15/507,328

(22) PCT Filed: Oct. 1, 2015

(86) PCT No.: PCT/US2015/053521
§ 371 (c)(1),
(2) Date: Feb. 28, 2017

(87) PCT Pub. No.: WO2016/054394
PCT Pub. Date: Apr. 7, 2016

(65) Prior Publication Data
US 2017/0284805 A1    Oct. 5, 2017

Related U.S. Application Data

(60) Provisional application No. 62/101,942, filed on Jan. 9, 2015, provisional application No. 62/058,517, filed on Oct. 1, 2014.

(51) Int. Cl.
*G01C 21/16* (2006.01)
*G01C 5/06* (2006.01)
(Continued)

(52) U.S. Cl.
CPC ............ *G01C 21/16* (2013.01); *A61B 5/1122* (2013.01); *A63B 5/16* (2013.01); *G01C 5/06* (2013.01);
(Continued)

(58) Field of Classification Search
CPC ......... A61B 5/1122; A63B 5/16; G01C 21/16; G01C 21/165; G01C 21/24; G01C 21/28; G01C 5/06; G01P 15/13
(Continued)

(56) References Cited

U.S. PATENT DOCUMENTS 4,882,697 A    11/1989  Ross
6,205,400 B1 *  3/2001  Lin .................... G01C 21/165
                                                342/357.31
(Continued)

FOREIGN PATENT DOCUMENTS

CN    203116727 U    8/2013
CN    103528565 A    1/2014
(Continued)

OTHER PUBLICATIONS

International Preliminary Report on Patentability issued in PCT Application No. PCT/US2015/053521 dated Apr. 13, 2017; 6 pages.
(Continued)

*Primary Examiner* — Tyler J Lee
(74) *Attorney, Agent, or Firm* — Patent Capital Group (57) ABSTRACT

The present disclosure provides a jump detection system for inertial measurement unit (IMU) integrated with a barometric altimeter in the same device (IMU-baro). The processor is configured to record time-series data of both a vertical component of the measured IMU-baro acceleration and the estimated vertical velocity of the IMU-baro, detect a potential jump by comparing the vertical component of the measured IMU-baro acceleration to one or more accelera-
(Continued)

tion thresholds, and, validate the potential jump by comparing a difference between a maximum velocity and a minimum velocity within a vicinity of the potential jump in the time-series data of the estimated vertical velocity of the IMU-baro to a velocity threshold.

15 Claims, 5 Drawing Sheets

(51) Int. Cl.
| | |
|---|---|
| *A61B 5/11* | (2006.01) |
| *A63B 5/16* | (2006.01) |
| *G01C 21/24* | (2006.01) |
| *G01C 21/28* | (2006.01) |
| *G01P 15/13* | (2006.01) |

(52) U.S. Cl.
CPC .......... *G01C 21/165* (2013.01); *G01C 21/24* (2013.01); *G01C 21/28* (2013.01); *G01P 15/13* (2013.01)

(58) Field of Classification Search
USPC ........................................................ 701/504
See application file for complete search history.

(56) References Cited

U.S. PATENT DOCUMENTS

| | | |
|---|---|---|
| 6,246,960 B1 | 6/2001 | Lin |
| 6,298,287 B1 | 10/2001 | Tazartes et al. |
| 6,882,308 B2 | 4/2005 | Etienne |
| 8,224,575 B2* | 7/2012 | Faulkner ............... G01C 21/16 340/988 |
| 8,862,394 B2* | 10/2014 | Taylor, Jr. ............... G01C 21/16 701/470 |
| 2004/0054470 A1 | 3/2004 | Farine et al. |
| 2006/0206267 A1 | 9/2006 | Kirkland et al. |
| 2007/0072158 A1 | 3/2007 | Unuma et al. |
| 2008/0077326 A1* | 3/2008 | Funk .................... G01C 21/165 701/500 |
| 2009/0007661 A1 | 1/2009 | Nasiri et al. |
| 2010/0204615 A1 | 8/2010 | Kyle et al. |
| 2011/0238307 A1 | 9/2011 | Psiaki et al. |
| 2011/0238308 A1* | 9/2011 | Miller .................... G01C 21/28 701/472 |
| 2013/0044043 A1 | 2/2013 | Abdollahi et al. |
| 2013/0130843 A1* | 5/2013 | Burroughs ........ A63B 71/0686 473/415 |
| 2013/0274587 A1 | 10/2013 | Coza et al. |
| 2013/0346013 A1 | 12/2013 | Lokshin et al. |
| 2014/0207374 A1* | 7/2014 | Taylor, Jr. .............. G01C 21/16 701/470 |
| 2014/0297008 A1* | 10/2014 | Perkins .............. G06K 9/00342 700/91 |
| 2017/0307376 A1 | 10/2017 | Zihajehzadeh et al. |

FOREIGN PATENT DOCUMENTS

| | | |
|---|---|---|
| WO | 2002039138 A1 | 5/2002 |
| WO | 2002046699 A1 | 6/2002 |
| WO | 2010025294 A1 | 3/2010 |

OTHER PUBLICATIONS

International Search Report and Written Opinion issued in PCT Application No. PCT/US2015/053517 dated Jan. 7, 2016.
International Search Report and Written Opinion issued in PCT Application No. PCT/US2015/053521 dated Jan. 13, 2016.
Extended European Search Report in European Patent Application No. 15846175.6 dated Apr. 3, 2018, 7 pages.
Non Final Office Action in U.S. Patent Application No. P88391US dated Jun. 15, 2018, 4 pages.
Zihajehzadeh, Shaghayegh et al., "Integration of MEMS Intertial and Pressure Sensors for Vertical Trajectory Determination," IEEE Transaction on Instrumentation and Measurement, vol. 64, No. 3, Mar. 2015, pp. 804-814 (11 pages).
Chinese Patent Office First Office Action in Chinese Patent Application No. 201580046983.5 dated Aug. 17, 2018 with Summary of Relevance, 6 pages.
Notice of Allowance in U.S. Appl. No. 15/507,549 dated Oct. 11, 2018, 7 pages.
Extended European Search Report in European Patent Application No. 15845616.0 dated May 23, 2018, 7 pages.
Krach, Bernhard et al, "Cascaded Estimation Architecture fro Integration of Foot-Mounted Inertial Sensors", PLANS 2008—Proceedings of IEEE/ION Plans 2008, The Institute of Navigation, 8551 Rixlew Lane, Suite 360, Manassas, VA 20109, May 8, 2008 (May 8, 2008), pp. 112-119.
Zihajehzadeh S., et al., "A cascaded two-step Kalman filter for estimateion of human body segment orientation using MEMS-IMU", 2014 36th Annual International Conference of the IEEE Engineering in Medicine and Biology Society, IEEE, Aug. 26, 2014 (Aug. 26, 2014), pp. 6270-273.

* cited by examiner

METHODS AND SYSTEMS FOR VERTICAL TRAJECTORY DETERMINATION AND AUTOMATIC JUMP DETECTION

CROSS REFERENCE TO RELATED APPLICATIONS

This application is a national stage application under 35 U.S.C. § 371 of PCT International Application Serial No. PCT/US2015/053521, filed on Oct. 1, 2015 and entitled "METHODS AND SYSTEMS FOR VERTICAL TRAJECTORY DETERMINATION AND AUTOMATIC JUMP DETECTION", which application claims the benefit of U.S. Provisional Application No. 62/058,517 titled "METHODS AND SYSTEMS FOR VERTICAL TRAJECTORY DETERMINATION" and filed on Oct. 1, 2014 and U.S. Provisional Application No. 62/101,942 filed "METHODS AND SYSTEMS FOR VERTICAL TRAJECTORY DETERMINATION AND AUTOMATIC JUMP DETECTION" and filed on Jan. 9, 2015, and are considered part of and are hereby incorporated by reference in their entireties in the disclosure of this application.

FIELD

The present disclosure relates to inertial navigation systems including MEMS inertial measurement units, and other systems for capturing and tracking human movement in vertical direction.

BACKGROUND

Key performance variables (KPVs) are quantitative measurements of an athlete's performance. By accessing and reviewing an athlete's KPVs, the athlete can significantly improve overall performance: KPVs allow the athlete to share performance information with coaches, record and track performance over time, and provide real-time feedback to the athlete.

In sports such as skiing and snowboarding, KPVs can describe the performance of jumps. The KPV of a jump may comprise: 1) the air-time (duration of the jump from take-off to landing), 2) the distance (horizontal displacement of the athlete from take-off to landing), 3) the height (maximum vertical height the athlete achieves), and 4) the degree of rotation (the rotation athletes achieved during jumps). These KPVs can be used to provide feedback and motivation to the athlete.

Currently available video-based or camera-based motion capture (MOCAP) approaches provide few quantitative variables. Additionally, these MOCAP techniques are restricted to indoor use or confined areas that are not suitable for motion capture of outdoor sports such as skiing, snowboarding, rollerblading and biking since these activities take place over large distances.

Inertial navigation systems (INS), on the other hand, are self-contained and thus can provide unconstrained accessibility to advanced motion and location information. INS is widely used in various MOCAP applications such as ship and aircraft navigation, fastening tool and pen tracking, and sports analysis to provide information such as attitude, velocity, and position.

Recently, miniature micro-electromechanical systems (MEMS) inertial devices have become more common, and the small size of MEMS inertial devices has resulted in the emergence of INS for human body motion tracking using wearable MOCAP technology. Typically, wearable MOCAP devices make use of a MEMS inertial measurement unit (MEMS-IMU) and/or an absolute position sensor to capture motion for indoor/outdoor localization. For example, a MOCAP camera system can act as an absolute position sensor and be added to inertial devices for more accurate human body localization in an indoor environment. For outdoor environments, a global positioning system (GPS) is an exemplary absolute position sensor that can be used to augment an inertial measurement unit for more accurate human body localization.

A disadvantage in the above mentioned GPS/MEMS-IMU integration approaches is that the consumer grade GPS-derived vertical positional (or altitude) information is typically much less accurate than the horizontal positional information. GPS altitude measurement accuracies can vary up to 40 m (with 10 m to 20 m being common); the most important reasons for this inaccuracy are satellite visibility (i.e. few visible satellites over the horizon) as well as multipath signal effects. Real-time GPS technologies such as real-time kinematic GPS and differential GPS provide higher positional accuracies but their prohibitive cost is a limiting factor for the sport consumer electronics market.

BRIEF DESCRIPTION OF THE DRAWINGS

Other aspects and features of the present disclosure will become apparent to those ordinarily skilled in the art upon review of the following description of specific embodiments in conjunction with the accompanying figures.

Embodiments of the present disclosure will now be described, by way of example only, with reference to the attached Figures.

DETAILED DESCRIPTION

Figure 1:
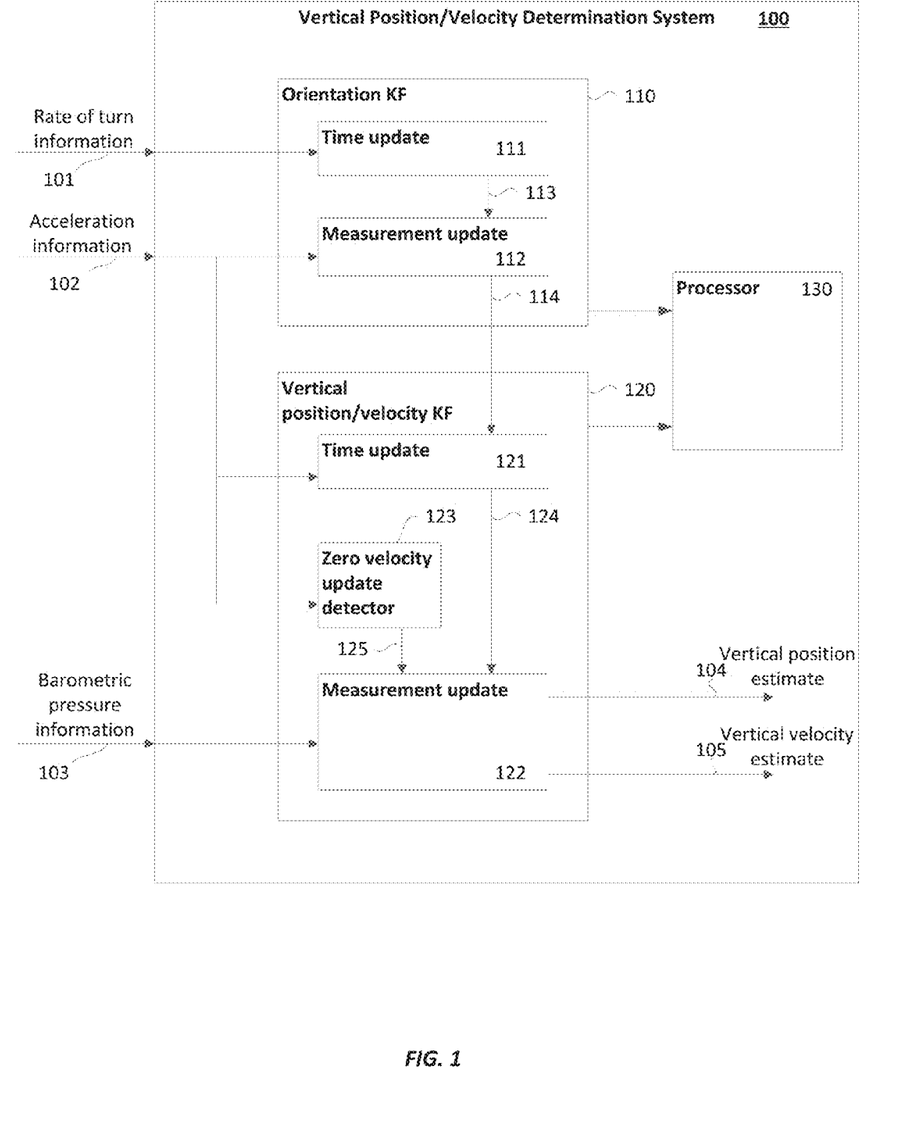
FIG. 1 is a block diagram of a vertical position determination system according to an embodiment of the present disclosure.

FIG. 1 shows a block diagram of an exemplary vertical position and velocity determination system 100 according to an embodiment of the present disclosure. As described below, the system 100 may provide increased computational efficiency in some embodiments, and may be implemented in a wearable electronic device to provide vertical motion information to the wearer of the device.

The system 100 includes inputs for receiving rate of turn information 101, acceleration information 102, and barometric pressure information 103. The rate of turn information input 101 may, for example, be connected to a gyroscope such as a tri-axial gyroscope (shown in FIG. 5 as part of MEMS-IMU 504). The acceleration information input 102 may, for example, be connected to an accelerometer such as a tri-axial accelerometer (shown in FIG. 5 as part of MEMS-IMU 504). The barometric pressure information input 103 may, for example, be connected to a barometric altimeter (shown in FIG. 5 as MEMS Barometric Altimeter 502). The system 100 may be used in conjunction with an inertial measurement unit (IMU) providing the accelerometer and the gyroscope, and also having a barometric altimeter integrated therewith. As used herein, the term "IMU-baro" is used to refer to such an IMU with an integrated barometric altimeter. The system 100 also includes a vertical position estimate output 104 and a vertical velocity estimate output 105.

The vertical position and velocity determination system 100 further comprises a cascaded two-step Kalman filter (KF) system including an orientation KF 110 and vertical position/velocity KF 120. The output of the first step (orientation KF 110) is provided as an input to the second step (vertical position/velocity KF 120).

The orientation KF 110 includes a gravity vector time-updater 111 and a gravity vector measurement-updater 112. The gravity vector time-updater 111 generates a prediction 113 of the gravity vector in the sensor frame (the coordinate frame of the IMU-baro) from the rate of turn information input 101. The gravity vector measurement-updater 112 generates a corrected gravity vector in the sensor frame from a weighted combination of both the gravity vector prediction 113 and the acceleration information input 102. Then, using the corrected gravity vector in the sensor frame, the gravity vector measurement-updater 112 generates roll and pitch angles information 114. As used herein, the term "roll angle" refers to rotation about a horizontal axis along a first (e.g. front-back) direction and the term "pitch angle" refers to rotation about a horizontal axis along a second (e.g. left-right) direction perpendicular to the first direction.

The vertical position/velocity KF 120 includes a vertical position/velocity time-updater 121, a vertical position/velocity measurement-updater 122, and an optional zero velocity update detector 123. The vertical position/velocity time-updater 121 generates a vertical position/velocity prediction 124 from the roll and pitch angles information 114 and the acceleration information input 102.

The vertical position/velocity measurement-updater 122 generates a corrected vertical position estimate 104 and a vertical velocity estimate 105 based on a weighted combination of the vertical position/velocity prediction 124 and the barometric pressure information input 103.

The optional zero velocity update detector 123 generates a zero velocity signal 125 from the acceleration information input 102. The zero velocity signal 125 forces the vertical velocity estimate 105 to zero when still phases are detected by the zero velocity update detector 123.

An INS estimates navigation parameters including position and velocity by solving strapdown inertial navigation equations though integration of the external acceleration values. Thus, it is important for the INS to accurately estimate external acceleration during dynamic conditions by subtracting the gravitational acceleration from the accelerometer signal. To realize this subtraction function, the INS requires an accurate estimation of its orientation.

The embodiment of FIG. 1 includes a cascaded KF in the form of an orientation KF cascaded with a vertical position/velocity KF. The cascaded KF provides good computation efficiency. The cascaded KF has much less computational overhead than a global KF because the calculations related to the orientation states are separated from the vertical position/velocity KF. Thus, the cascaded KF can be implemented using linear functions whereas the global KF would require non-linear Kalman filtering methods such as those utilized by an extended Kalman filter (EKF) or an unscented Kalman filter (UKF). In addition to the improved computational cost, the cascaded KF allows for increased flexibility and easier implementation and tuning over the global KF.

Though the cascaded KF theoretically produces sub-optimal (less accurate) estimates compared to the global KF, in practice for the purpose of inertial navigation, the performance of the cascaded KF is positively comparable to the global KF. Preliminary testing of an example cascaded KF system according to examples disclosed herein indicates that the vertical trajectory tracking error is about 26.9 cm, 27.2 cm and 28.1 cm for slow motion, vertical jump and step-down jumps vertical trajectory tracking respectively. Details of the experimental setup and further results from the preliminary testing are set forth in the paper attached as Appendix A.

Significant improvement in vertical trajectory tracking accuracy was observed with the use of a Rauch-Tung-Striebel (RTS)-smoother, as discussed below. Additionally, based on the experimental results, the average jump KPVs (height/drop) determination error with the use of an RTS-smoother is about 2.9 cm and 5.8 cm for vertical jump and step-down jump respectively (compared to the ~40 m error of the GPS in some spots in the vertical direction). This achieved accuracy should be sufficient for recreational purposes where the magnitude of jump height is small. On the other hand, the magnitude of jump height in athletic sport jumps is much higher than the one in recreational jumps. As a result, the achieved jump KPVs determination accuracy of about 2.9~5.8 cm should also be adequate for outdoor measurement purposes using wearable technologies.

The structures of the individual filters in the cascaded KF, i.e. the orientation KF 110 and the vertical position/velocity KF 120, will now be described. In the following description, subscripts 1 and 2 refer to the variables of the orientation KF 110 and the vertical position/velocity KF 120, respectively.

The orientation KF 110 generates roll and pitch angles information 114. The roll and pitch angles information 114 is sufficient for gravitation acceleration compensation and inertial motion tracking in vertical direction. Thus, information of a full three-dimensional orientation is not required.

Tri-axial gyroscopes and tri-axial accelerometers provide rate of turn information inputs 101 and acceleration information inputs 102, respectively, to the orientation KF 110. The gravity vector time-updater 111 performs the function of Equation 1, below, to generate a prediction 113 of the gravity vector in the sensor frame from the rate of turn information input 101.

$$x_1(k) = A_1(k-1)x_1(k-1) + w_1(k-1) \quad \text{(Equation 1)}$$

In Equation 1, $x_1(k)$ is the 3×1 state vector for orientation KF 110 at step k; thus, $x_1(k)$ is the normalized gravity vector in the sensor frame; $A_1$ is the state transition matrix; and $w_1$ is the process model noise vector. The gravity vector time-updater 111 generates the prediction 113 of the gravity vector in the sensor frame, $x_1(k)$, from a predictive model using a previous gravity vector prediction, $x_1(k-1)$.

The gravity vector measurement-updater 112 performs the function of Equation 2, below, to the update the gravity vector prediction 113 with measurements from the acceleration information input 102.

$$z_1(k) = C_1(k)x_1(k) + v_1(k) \quad \text{(Equation 2)}$$

In Equation 2, $z_1$ is the measurement vector (i.e. the gravity vector measured in the sensor frame of the accelerometers); $C_1$ is the 3×3 observation matrix; and $v_1$ is the measurement model noise vector.

The matrices of Equations 1 and 2 are calculated from Equations 3 to 13, below.

Generating the Gravity Vector Prediction of the Orientation KF $$A_1(k-1) = I_3 - \Delta t \tilde{y}_G(k-1) \quad \text{(Equation 3)}$$

The state transition matrix, $A_1(k-1)$, is derived from $I_3$, which is a 3×3 identity matrix; and $\tilde{y}_G$, which is the 3×3 skew symmetric matrix of tri-axial gyroscope measurements.

$$w_1(k-1) = \Delta t(-\tilde{x}_1(k))n_G \quad \text{(Equation 4)}$$

The process model noise vector $w_1(k-1)$, is based on $\tilde{x}_1$, which is a 3×3 skew symmetric matrix of $x_1$; and $n_G$, which is the gyroscope measurement noise vector, and is assumed to be uncorrelated and zero-mean white Gaussian.

Thus, Equations 1, 3 and 4 define the gravity vector prediction 113. In this way, the gravity vector time-updater 111 derives $x_1(k)$, the gravity vector prediction 113, from $\tilde{y}_G$, the rate of turn information input 101.

Generating the Roll and Pitch Angles Information of the Orientation KF $$C_1(k) = gI_3 \quad \text{(Equation 5)}$$

In Equation 5, $C_1$, the 3×3 observation matrix, is derived from $I_3$, which is a 3×3 identity matrix; and g, which is the norm of gravity vector.

$$v_1(k) = -{}^s a_\varepsilon^-(k) + n_A \quad \text{(Equation 6)}$$

In Equation 6, $v_1$, the measurement model noise vector, is derived from ${}^s a_\varepsilon^-(k)$, which is the external acceleration error in the sensor frame of the accelerometer; and $n_A$, which is the gyroscope measurement noise vector, and is assumed to be uncorrelated and zero-mean white Gaussian.

Equations 7 and 8 describe the external acceleration error in the sensor frame of the accelerometer.

$$ {}^s a_\varepsilon^-(k) = {}^s a^-(k) - {}^s a(k) \quad \text{(Equation 7)}$$

$$ {}^s a^-(k) = c_\alpha {}^s a^+(k-1) \quad \text{(Equation 8)}$$

In Equation 7, ${}^s a(k) = c_\alpha {}^s a(k-1) + \varepsilon(k)$, with $\varepsilon(k)$ being the time-varying error of the external acceleration process model. In Equations 7 and 8, the superscripts + and − stand for the "a posteriori" and the "a priori" estimates in the orientation KF 110, respectively; the superscript S denotes that the quantity is in the sensor frame; $c_\alpha$ is a dimensionless constant between 0 and 1 that determines the cut-off frequency in the external acceleration model.

$$z_1(k) = y_A(k) - C_\alpha {}^s a^+(k-1) \quad \text{(Equation 9)}$$

$$ {}^s a^+(k) = y_A(k) - g x_1^+(k) \quad \text{(Equation 10)}$$

The measurement vector, $z_1$, in Equation 2 is defined by Equations 9 and 10, where $y_A(k)$ is the bias compensated output vector of the accelerometer; and the estimated normalized gravity vector in the sensor frame is $x_1^+(k)$. Thus, Equations 2 and 5-10 define the estimated normalized gravity vector in the sensor frame, $x_1^+(k)$.

$$\gamma = \tan^{-1}\left(\frac{x_{1,y}}{x_{1,z}}\right), \beta = \tan^{-1}\left(\frac{-x_{1,x}}{x_{1,y}/\sin\gamma}\right) \quad \text{(Equation 11)}$$

Equation 11 uses the estimated normalized gravity vector in the sensor frame, $x_1^+(k) = [x_{1,x} \ x_{1,y} \ x_{1,z}]^T$, to generate calculated roll ($\gamma$) and pitch ($\beta$) angles. According to Equations 2 and 5-11, the gravity vector measurement-updater 112 generates an orientation signal 114 indicating roll ($\gamma$) and pitch ($\beta$) angles from $y_A(k)$, the acceleration information input 102, and from $x_1(k)$, the gravity vector prediction 113.

$$Q_1(k-1) = -\Delta t^2 \tilde{x}_1(k-1) \Sigma_G \tilde{x}_1(k-1) \quad \text{(Equation 12)}$$

$$R_1(k) = \Sigma_{acc} + \Sigma_A \quad \text{(Equation 13)}$$

Equations 12 and 13 define the process and measurement noise covariance matrices in the orientation KF 110. Process noise covariance matrix $Q_1(k-1)$ is calculated using the process model noise vector $w_1(k-1)$ and is equal to $E[w_1(k-1)w_1(k-1)^T]$ where E is the expectation operator. $\Sigma_G$ is the covariance matrix of the gyroscope's measurement noise which is defined as $E[n_G n_G^T]$. By assuming that the gyro noise variances are equal to $\sigma_G$ in the three axes, $\Sigma_G$ is set to $\sigma_G^2 I_3$.

Measurement noise covariance matrix $R_1(k)$ is calculated using the measurement model noise vector $v_1(k)$ and is equal to $E[V_1(k)V_1(k)^T]$. $\Sigma_A$, which is the covariance matrix of accelerometer's measurement noise, is set to $\sigma_A^2 I_3$. $\Sigma_{acc}$ is the covariance of the acceleration model and is set to $3^{-1} c_\alpha^2 \|{}^s a^+(k-1)\|^2$.

Generating the Vertical Position/Velocity Prediction of the Vertical Position/Velocity KF The vertical position/velocity KF 120 generates the vertical position estimate 104 and the vertical velocity estimate 105. The orientation KF 110, the tri-axial accelerometers, and a barometric altimeter, provide roll ($\gamma$) and pitch ($\beta$) angles (from orientation signal 114), acceleration information (from input 102), and the barometric pressure information (from input 103) respectively, to the vertical position/velocity KF 120.

The vertical position/velocity time-updater 121 performs the function of Equation 14, below, to generate the vertical position/velocity prediction 124 from the roll and pitch angles from orientation signal 114 and the acceleration information from input 102.

$$x_2(k) = A_2(k-1)x_2(k-1) + B_2(k-1)u_2(k-1) + w_2(k-1) \quad \text{(Equation 14)}$$

In Equation 14, $x_2(k) = [h(k) \ v(k)]^T$ is the state vector for the vertical position/velocity KF 120, including vertical position and vertical velocity components; $A_2(k-1)$ and $B_2(k-1)$ are the state transition and input matrices for the vertical position/velocity KF 120; $u_2(k-1)$ is the input vector, which includes the vertical component of gravity compensated acceleration in the navigation frame, and is calculated using inputs 102 and 114; $w_2(k-1)$ is the 2×1 vector of process noise.

$$A_2(k-1) = \begin{bmatrix} 1 & \Delta t \\ 0 & 1 \end{bmatrix} \quad \text{(Equation 15)}$$

$$B_2(k-1) = \begin{bmatrix} \frac{1}{2}\Delta t^2 \\ \Delta t \end{bmatrix} \quad \text{(Equation 16)}$$

Equations 15 and 16 define the state transition and input matrices $A_2(k-1)$ and $B_2(k-1)$, respectively.

$$u_2(k-1) = ([0 \ 0 \ 1]) \cdot ({}_s^n R_{\gamma,\beta} y_A(k-1) + [0 \ 0 \ g]^T) \quad \text{(Equation 17)}$$

Equation 17 defines the vertical component of gravity compensated acceleration in the navigation frame. The value of the vertical component of gravity compensated acceleration in the navigation frame is based on the rotation matrix, ${}_s^n R_{\gamma,\beta}$ which is calculated using roll ($\gamma$) and pitch ($\beta$) angles from the orientation signal 114 and the acceleration from input 102, $y_A(k-1)$. $_s^n R_{\gamma,\beta}$ aligns the z-axis of the accelerometer sensor frame to the navigation frame;

$$_s^n R_{\gamma,\beta} = \begin{bmatrix} \cos\beta & 0 & \sin\beta \\ 0 & 1 & 0 \\ -\sin\beta & 0 & \cos\beta \end{bmatrix} \begin{bmatrix} 1 & 0 & 0 \\ 0 & \cos\gamma & -\sin\gamma \\ 0 & \sin\gamma & \cos\gamma \end{bmatrix} \quad \text{(Equation 18)}$$

$$w_2(k-1) = \begin{bmatrix} \frac{1}{2}\Delta t^2 \\ \Delta t \end{bmatrix} \sigma_A \quad \text{(Equation 19)}$$

Equations 18 and 19 describe the rotation matrix, $_s^n R_{\gamma,\beta}$, that aligns the z-axis of the accelerometer sensor frame to the navigation frame; and the 2×1 vector of process noise, $w_2(k-1)$, respectively.

According to Equations 14 to 19, the vertical position/velocity time-updater 121 generates $x_2(k)$, the vertical position/velocity prediction 124, from the roll ($\gamma$) and pitch ($\beta$) angles from the orientation signal 114 and the acceleration information input 102.

Generating the Vertical Position Estimate and Vertical Velocity Estimate of the Vertical Position/Velocity KF The vertical position/velocity measurement-updater 122 performs the function of Equation 20, below, to generate the vertical position estimate 104 and the vertical velocity estimate 105 from the vertical position/velocity prediction 124 and the barometer information input 103.

$$z_2(k) = C_2(k)x_2(k) + v_2(k) \quad \text{(Equation 20)}$$

In Equation 20, $z_2(k)$ is the relative height ($\Delta h_{baro}$), which is calculated from the barometer information input 103; $C_2(k)$ is the observation matrix; and $v_2(k)$ is the measurement noise.

$$z_2(k) \triangleq \Delta h_{baro} = 44330\left(1 - \left(\frac{P}{P_0}\right)^{0.19}\right) - h_{init} \quad \text{(Equation 21)}$$

Equation 21 describes how the barometer information input 103, P, is used in the vertical position/velocity measurement-updater 122. In Equation 21, $\Delta h_{baro}$ is the relative height with respect to the initial height ($h_{init}$) of a reference position; $h_{init}$ is calculated using the initial pressure data at a reference position, ($h_{init}$ may be calculated, for example using stationary initialization as discussed below; and $P_0$ is the standard pressure equal to 101,325 Pa. Due to the significant quantization noise present in the barometric altimeter, a rolling average filter should be used to increase the accuracy of the barometric height measurement and its remaining residual errors should be taken into account in the measurement noise, $v_2(k)$.

$$C_2(k) = [1\ 0] \quad \text{(Equation 22)}$$

Equation 22 defines the observation matrix $C_2(k)$.

$$Q_2(k-1) = B_2(k-1)E[w_2(k-1)w_2(k-1)^T] \quad \text{(Equation 23)}$$
$$B_2(k-1)^T$$
$$= \begin{bmatrix} \frac{1}{2}\Delta t^2 \\ \Delta t \end{bmatrix} \sigma_A^2 \begin{bmatrix} \frac{1}{2}\Delta t^2 \\ \Delta t \end{bmatrix}^T$$

Equation 23 defines the process noise covariance matrix $Q_2(k-1)$ calculated using the process noise vector $w_2(k-1)$ and input matrix $B_2(k-1)$.

$$R_2(k) = \sigma_{baro}^2 \quad \text{(Equation 24)}$$

Equation 24 defines the measurement noise covariance matrix $R_2(k)$, where $\sigma_{baro}^2$ the barometer noise variance. The measurement noise covariance matrix $R_2(k)$ is obtained by $E[v_2(k)v_2(k)^T]$.

According to Equations 20 to 24, the vertical position/velocity measurement-updater 122 corrects $x_2(k) = [h(k)\ v(k)]^T$, the vertical position/velocity prediction 124, with $z_2(k)$, a relative height measurement derived from the barometer information input 103, to generate the vertical position estimate 104, h(k), and the vertical velocity estimate 105, ḣ(k).

The vertical position/velocity determination system of FIG. 1 advantageously provides an accurate estimate of a relative height measurement without the use of a GPS. Therefore, the vertical position and velocity determination system 100 can be combined with a GPS/MEMS-IMU to augment the GPS/MEMS-IMU with improved vertical position determination. The vertical position and velocity determination system 100 is particularly complementary to the GPS/MEMS-IMU since, in a steady state, the GPS can be used to initialize (to an absolute height) the barometric altimeter of the vertical position determination system; whereas, in a dynamic state, the vertical position and velocity determination system 100 can provide an accurate estimate of the relative height measurement, without reliance on the inaccurate dynamic height measurement of the GPS.

In a further embodiment of FIG. 1, the vertical position and velocity determination system 100 optionally includes a zero velocity update detector 123 to limit the drift error in the INS. The optional zero velocity update detector 123 generates a zero velocity signal 125 from the acceleration information input 102. The zero velocity signal 125 forces the vertical velocity estimate 105 to zero when still phases are detected by the zero velocity update detector 123. In some embodiments, still phases are detected by setting a threshold on the norm of acceleration signal measured by the accelerometers, and determining a still phase when the acceleration signal is below the threshold.

In some embodiments, stationary initialization may be used to calibrate the vertical position and velocity determination system 100. During stationary initialization, initial attitude and sensor biases are calculated. The tri-axial accelerometer and tri-axial gyroscope data are used in the orientation KF 110 to calculate the average value of initial tilt angles. The external acceleration in the sensor frame, $^s a^+(k)$, is the by-product of the orientation KF 110. However, since the external acceleration should be zero during the stationary initialization step, the average value of $^s a^+(k)$ is considered as the accelerometer bias vector in the sensor frame. Assuming that MEMS gyroscopes are not accurate enough to measure earth's rotation rate, the gyro bias vector is calculated as the mean value of the tri-axial gyroscope measurement during this stationary initialization step. These bias values are assumed to be constant during the operational periods between stationary initialization procedures. The estimated accelerometer and gyroscope biases are then subtracted from the measured accelerometer and gyroscope signals for vertical trajectory estimation. During the stationary initialization step, velocity is set to zero and $h_{init}$ in the barometric altimeter is calibrated by initial height obtained from a reference system. This reference system can provide the actual ellipsoid height for absolute height tracking (such as the one obtained from GPS) or relative height with respect to an arbitarary coordinate system for relative height tracking (such as the one obtained from camera-based MOCAP system).

Figure 5:
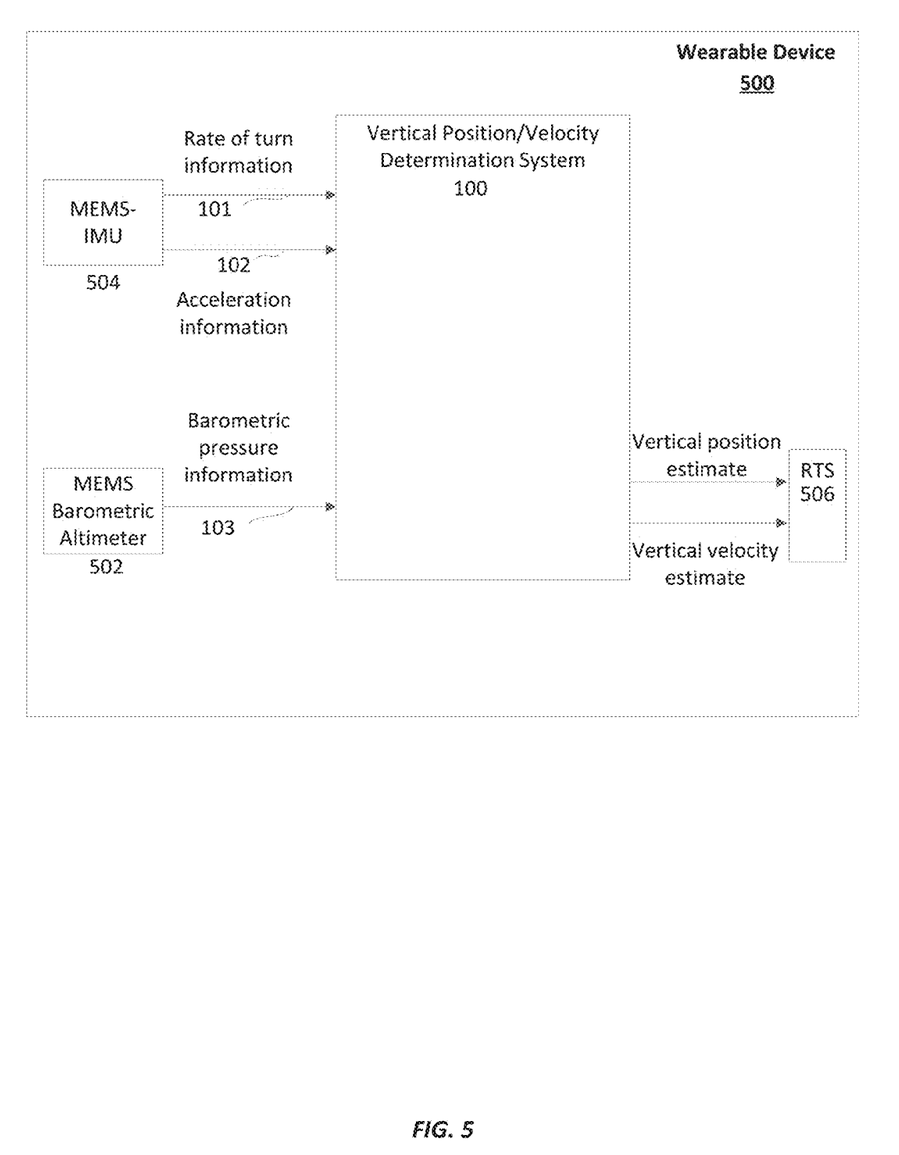
FIG. 5 is a schematic block diagram of an apparatus for vertical trajectory determination in accordance with embodiments of the present disclosure.

In yet a further embodiment of the present disclosure, the vertical position and velocity determination system 100 includes a trajectory smoother (shown in FIG. 5). In applications where real-time data processing is not required, the accuracy of the vertical position estimate can be further improved by smoothing, which combines forward and backward processed data. In an example, the trajectory smoother of the vertical position determination system 100 is configured as a Rauch-Tung-Striebel (RTS) trajectory smoother. The RTS smoother is a widely used trajectory smoother in navigation applications, for smoothing out position and velocity trajectories. The RTS smoother includes one forward data processing portion and one backward data processing portion. The forward processing portion of the RTS smoother is the vertical position/velocity KF 120 of the vertical position and velocity determination system 100. The RTS smoother stores the estimate and its covariance from the forward processing portion, and then recursively updates the smoothed estimate and its covariance in a backward sweep using the following Equations 25 to 27:

$$K_s(k) = P_2^+(k) A_2(k) [P_2^-(k+1)]^{-1} \quad \text{(Equation 25)}$$

$$P_s(k) = P_2^+(k) + K_s(k)[P_s(k+1) - P_2^-(k+1)] K_s(k)^T \quad \text{(Equation 26)}$$

$$x_s(k) = x_2^+(k) + K_s(k)[x_s(k+1) - x_2^-(k+1)] \quad \text{(Equation 27)}$$

In Equations 25 to 27, $P_2^+$ and $P_2^-$ are the "a posteriori" and the "a priori" covariance estimates; $K_s$ is the smoother gain; $x_2^+$ and $x_2^-$ are the "a posteriori" and the "a priori" state estimates; and $x_s$ is the smoothed state vector. All of the above mentioned variables relate to vertical position/velocity KF 120.

A processor 130 may be connected to the orientation KF 110 and vertical position/velocity KF 120. The processor 130 is configured to record time-series data of both a vertical component of the measured IMU-baro acceleration and the estimated vertical velocity of the IMU-baro, detect a potential jump by comparing the vertical component of the measured IMU-baro acceleration to one or more acceleration thresholds, and, validate the potential jump by comparing a difference between a maximum velocity and a minimum velocity within a vicinity of the potential jump in the time-series data of the estimated vertical velocity of the IMU-baro to a velocity threshold.

Figure 2:
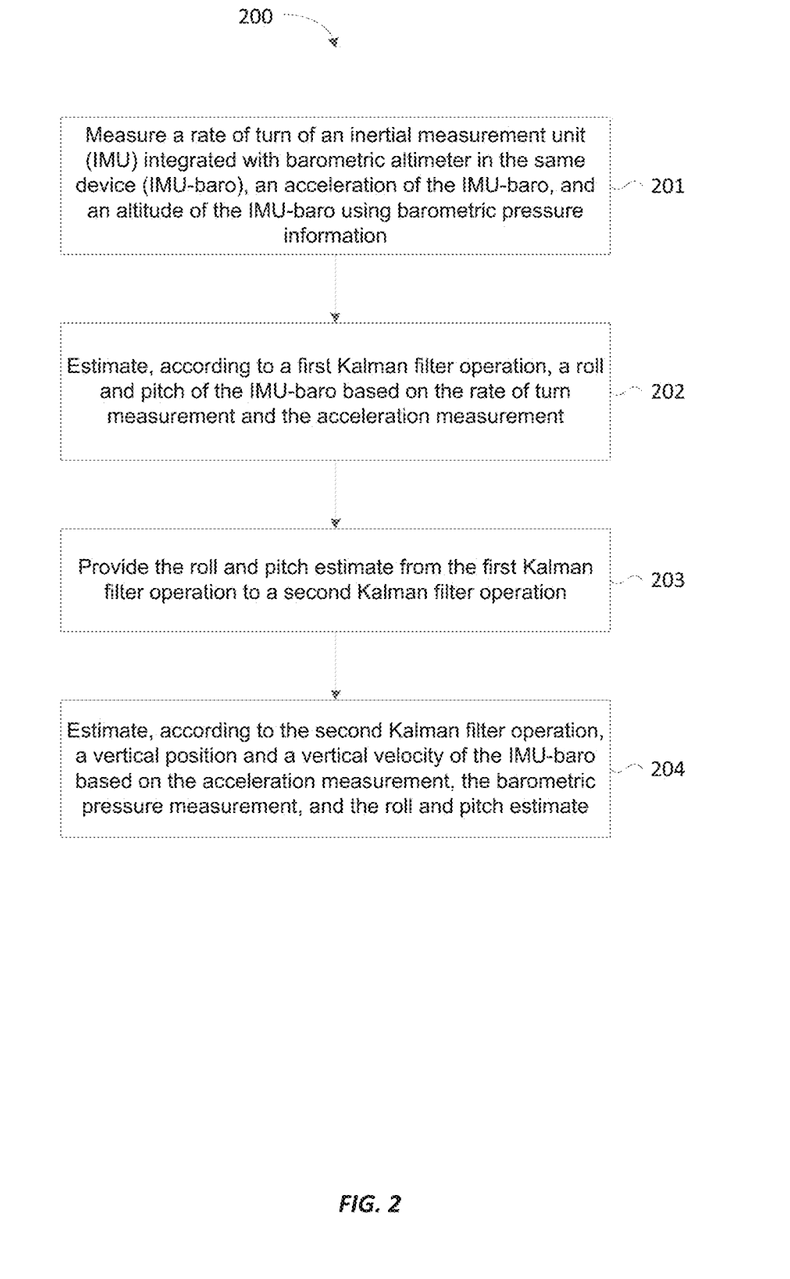
FIG. 2 is a flow chart diagram of a method of vertical position determination according to an embodiment of the present disclosure.

FIG. 2 shows a flow chart diagram of a method 200 of vertical position/velocity determination according to an embodiment of the present disclosure.

At 201, the method measures the rate of turn of an inertial measurement unit (IMU) integrated with barometric altimeter in the same device (IMU-baro), an acceleration of the IMU-baro, and an altitude of the IMU-baro using barometric pressure information from the barometric altimeter. In an embodiment, these measurements include noisy data; that is, the measurement value inherently includes errors such as errors caused by sensor noise.

At 202, the method estimates, according to a first Kalman filter operation, a roll and pitch of the IMU-baro based on the rate of turn measurement and the acceleration measurement. In an embodiment, estimating at 202 further includes recursively predicting and correcting steps in a Kalman filter.

Predicting includes predicting the gravitational acceleration vector in the IMU-baro sensor frame based on the strapdown integration using rate of turn measurement from gyroscope and the prior gravitational acceleration in the IMU-baro sensor frame. Correcting includes combining the prediction of the gravitational acceleration vector in the sensor frame with the measurement from the accelerometer to generate an estimate of the gravitational acceleration vector in the sensor frame. Finally, roll and pitch angle functions calculate the estimated roll and pitch angles from the estimated gravitational acceleration vector in the sensor frame.

At 203, the method provides the roll and pitch estimate from the first Kalman filter operation to a second Kalman filter operation. In embodiment, an output of the first Kalman filter operation is an input of the second Kalman filter operation.

At 204, the method estimates, according to the second Kalman filter operation, vertical position/velocity of the IMU-baro based on the acceleration measurement, the barometric pressure measurement, and the roll and pitch estimate. In an embodiment, estimating at 204 further includes recursively predicting and correcting in a Kalman filter.

Predicting includes predicting a vertical position (altitude) and a vertical velocity based on the strapdown integration using acceleration of the IMU-baro and the prior vertical position and vertical velocity.

Correcting includes combining, in a Kalman filter, the predicted vertical position and vertical velocity with the measured vertical position (altitude measurement) from the barometric altimeter to generate vertical position and vertical velocity estimates.

Figure 3:
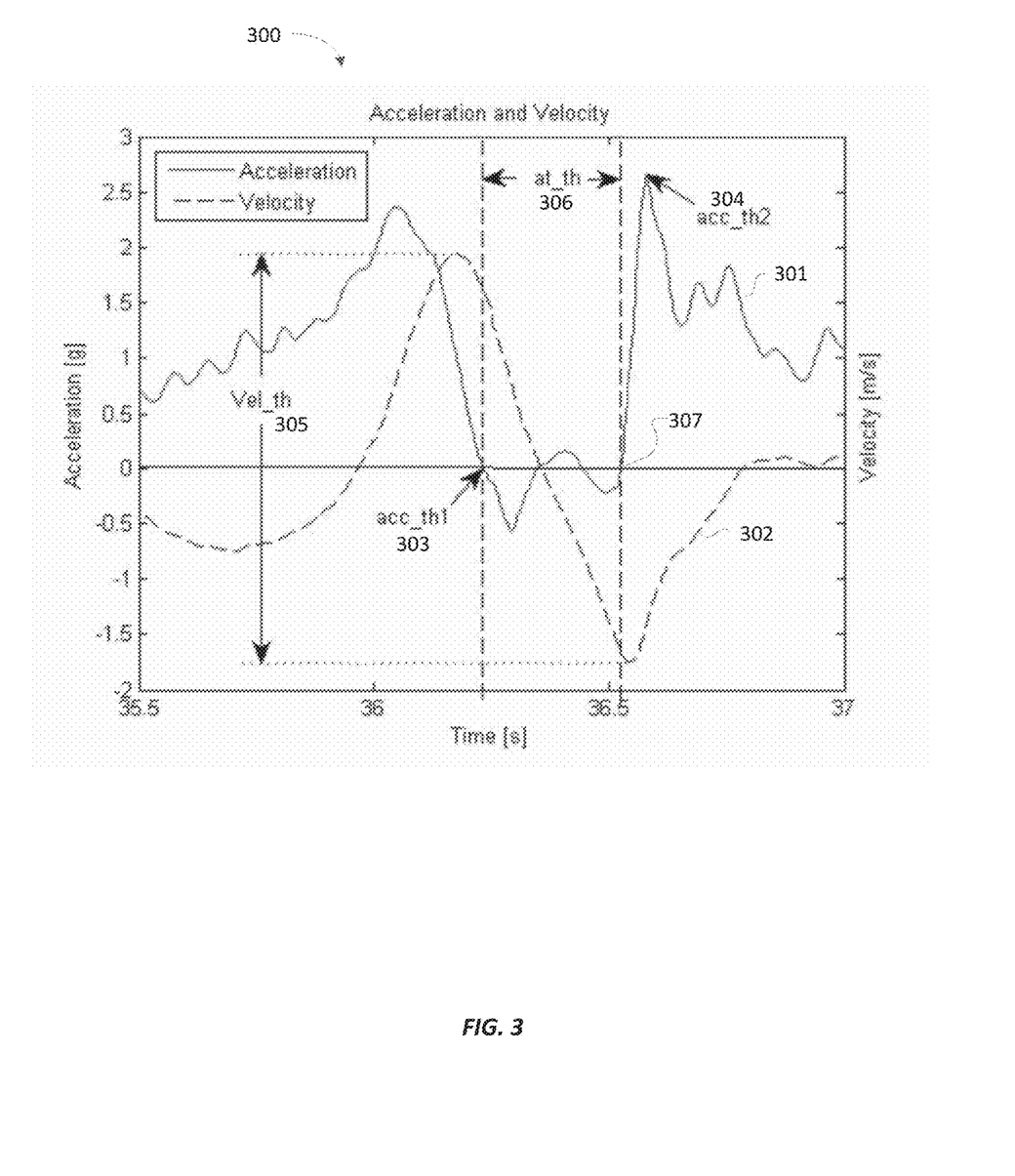
FIG. 3 is a graph showing threshold-processing vertical acceleration, vertical velocity, and time, according to an embodiment of present disclosure.

FIG. 3 is a graph showing example vertical acceleration and vertical velocity over time for an example jump. The solid line shows an example vertical acceleration signal 301 (normalized for gravity) from an IMU-baro device according to an embodiment of the present disclosure. The dashed line shows an example vertical velocity signal 302, which may, for example be an estimated velocity from an IMU-baro according to an embodiment of the present disclosure. FIG. 3 illustrates a number of characteristics of the acceleration and velocity signals 301 and 302 that may be compared to certain thresholds for automatic jump detection according to embodiments of the present disclosure, as discussed further below.

A takeoff indicator 303 in the acceleration signal 301 may be determined when the acceleration signal 301 drops below a first acceleration threshold (e.g, zero when the acceleration signal 301 is normalized for gravity), to indicate the start of a potential jump event.

A post-takeoff peak acceleration 304 in the acceleration signal 301 may be compared to a second acceleration threshold to indicate the end of a potential jump event when the vertical acceleration exceeds the second acceleration threshold. The second acceleration threshold is selected to correspond to typical jump landing forces measured by the device. The second acceleration threshold may, for example, be about 1 g or more. In some embodiments, the second acceleration threshold may be about 1.1 g. In some embodiments, the second acceleration threshold may be about 1.25 g.

A velocity difference 305 may be used to verify a potential jump as an actual jump. The velocity difference 305 may be determined as the difference between a local maximum in the velocity signal 302 at a time within a predetermined range of (e.g. just before) the takeoff indicator 303 in the acceleration signal 301, and a local minimum in the velocity signal 302 at a time within a predetermined range of the post-takeoff peak acceleration 304. The velocity difference 305 may be compared to a velocity threshold to verify a jump. The velocity threshold may be calibrated to correspond to a majority of typical jumps and eliminate false jumps. The velocity threshold may, for example, be about 3 m/s or more. In some embodiments, the velocity threshold may be about 3.1 m/s. In some embodiments, the velocity threshold may be about 4.3 m/s.

A jump time 306 may be used to verify a potential jump as an actual jump. The jump time 306 may be determined as the time between the takeoff indicator 303 and a zero crossing 307 in the acceleration signal 301 immediately prior to the post-takeoff peak acceleration 304. The jump time 306 may be compared to a jump time threshold to verify a jump. The jump time threshold may be calibrated to correspond to a majority of typical jumps and eliminate false jumps. The jump time threshold may, for example, be about 0.1 s or more. In some embodiments, the jump time threshold may be about 0.12 s. In some embodiments, the jump time threshold may be about 0.30 s.

Details of experiments conducted and further example thresholds are set forth in the paper attached as Appendix B.

Figure 4:
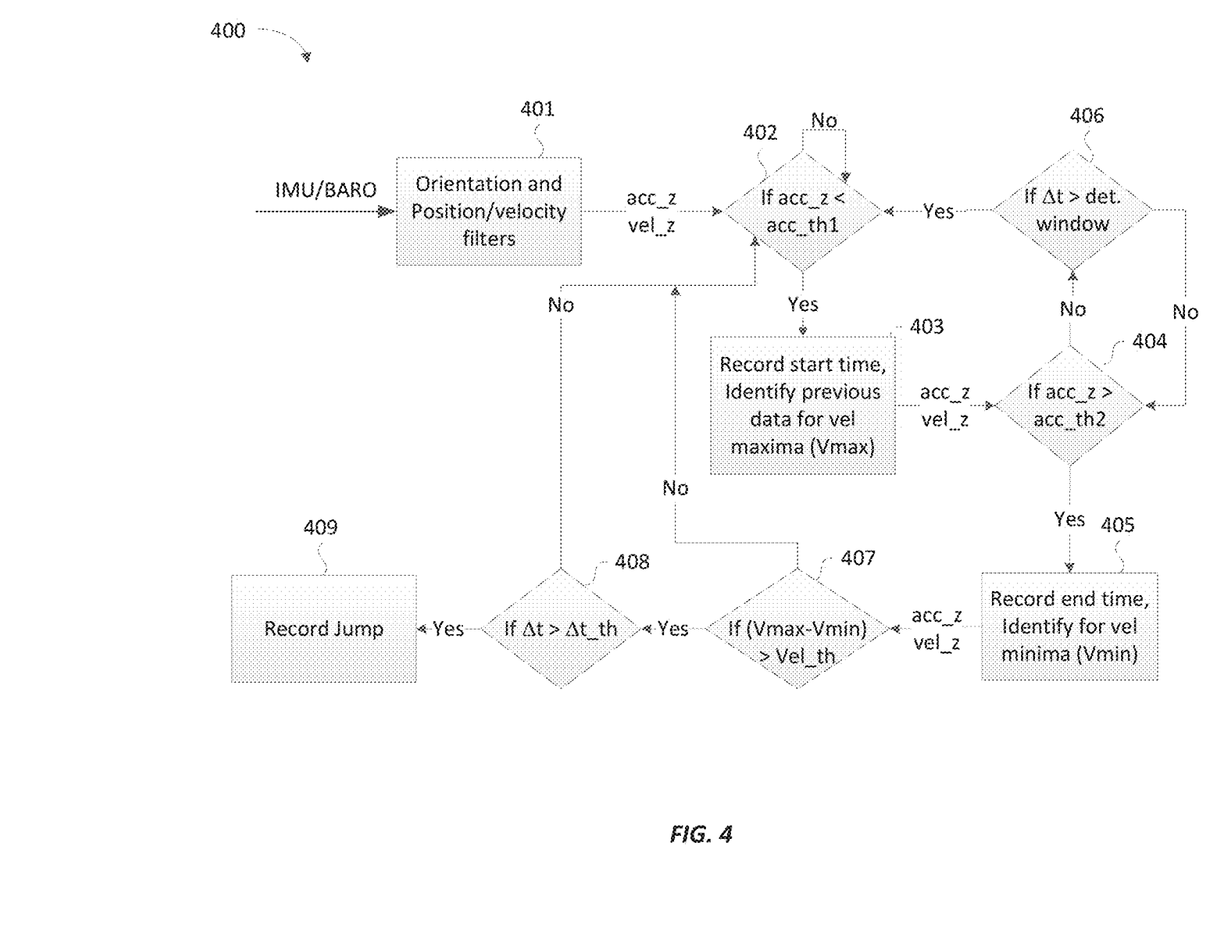
FIG. 4 is a flow chart diagram of a method of automatically detecting a jump event according to an embodiment of the present disclosure.

FIG. 4 shows a flow chart diagram of a method 400 of automatically detecting a jump event according to an embodiment of the present disclosure. The method 400 processes vertical acceleration and vertical velocity data to automatically detect a jump event by an athlete. The method 400 includes, receiving IMU, GPS and barometric pressure information at 401 to provide a measured IMU-baro acceleration signal 301 and an estimated vertical velocity signal 302. The acceleration and velocity signals 301 and 302 may, for example, be provided utilizing a system 100 as disclosed above. In some embodiments, the method 400 may also include receiving GPS information for initialization of an absolute height, as discussed above.

At 402, the method compares the measured IMU-baro acceleration signal 301 to the first acceleration threshold to identify a takeoff indicator 303 indicative of the start of a potential jump event. If the measured IMU-baro acceleration signal 301 remains higher than the first acceleration threshold, the method remains at 402 and keeps checking whether the measured IMU-baro acceleration 301 falls below the first acceleration threshold.

Once the measured IMU-baro acceleration 301 falls below the first acceleration threshold at 402, a potential jump is detected and the method proceeds to 403 to record a start time of the potential jump. At 403, the method further begins to validate the potential jump by searching for a local maximum in the estimated vertical velocity signal 302 of the IMU-baro previous to the recorded start time.

The method 400 then proceeds to 404, where it continues to monitor the measured IMU-baro acceleration signal 301 and the estimated vertical velocity signal 302 of the IMU-baro from the vertical position and velocity determination system 100. At 404 the method 400 compares the measured IMU-baro acceleration signal 301 to the second acceleration threshold indicative of the end of a jump event. The second acceleration threshold value is calibrated to correspond to typical jump landing forces. If the measured IMU-baro acceleration signal 301 exceeds the second acceleration threshold, the method identifies a landing and proceeds to 405. If the measured IMU-baro acceleration signal 301 does not exceed the second acceleration threshold, proceeds to 406 in order to keep checking whether the measured IMU-baro acceleration signal 301 exceeds the second acceleration threshold.

The method 400 will only keep checking whether the measured IMU-baro acceleration singal 301 exceeds the second acceleration threshold for as long as a predetermined time defined at 406. At 406 the method compares the elapsed jump time since the recorded start of jump to a first timer threshold. The first timer threshold is set to allow the method to identify a landing at 404 for only an amount of time that is reasonable for a typical jump. The first timer threshold may be varied depending on the context and the type(s) of jump expected. For example, preliminary test data indicates that jumps will typically have an airtime of at least 0.15 s. The first timer threshold may, for example, be in the range of about 0.1-0.3 s. In some embodiments, the jump time threshold may be about 0.12 s.

Once the total elapsed jump time exceeds the first timer threshold at 406, the method determines that the potential jump previously identified at 402 is invalid. A false jump could be detected at 402 due to measurement noise, for example, from the athlete's head movement. The method returns to 402 where the method continues to monitor the measured IMU-baro acceleration signal 301 in order to identify a future potential jump.

Referring back to 405, the method records an end time for the potential jump based on the time that the measured IMU-baro acceleration signal 301 exceeded the second acceleration threshold at 404. For example, recording the end time may include identifying a zero crossing 307 in the acceleration signal 301 immediately prior to exceeding the second acceleration threshold. At 405, the method 400 also searches for a minimum in the estimated vertical velocity signal 302 of the IMU-baro after the recorded end time.

The method then proceeds to 407 and compares the velocity difference 305 associated with the potential jump to the velocity threshold. The estimated velocity difference 305 is calculated by subtracting the minimum estimated vertical velocity 302 of the IMU-baro, identified at 405, from the maximum estimated vertical velocity 302 of the IMU-baro, identified at 403. A valid jump has a typical minimum velocity difference which may be selected as the velocity threshold; therefore, the method 400 compares the calculated estimated velocity difference 305 of the potential jump to the velocity threshold, which is calibrated to correspond to a majority of typical jumps and eliminate false jumps. If the calculated estimated velocity difference 305 is less than the velocity threshold, the method returns to 402 in order to continue to monitor the measured IMU-baro acceleration signal 301 to identify a future potential jump.

If the calculated estimated velocity difference 305 is greater than the velocity threshold, the method proceeds to 408 in order to compare the total elapsed time of the potential jump to the jump time threshold. The total elapsed jump time is calculated by subtracting the recorded start time from the recorded end time. The jump time threshold is calibrated to correspond to a majority of typical jumps and eliminate false jumps. If the total elapsed jump time is less than the jump time threshold, the method returns to 402 in order to continue to monitor the measured IMU-baro acceleration signal 301 to identify a future potential jump.

If, at 408, the total elapsed jump time is greater than the jump time threshold, the method determines that the potential jump detected at 402 is valid and proceeds to 409 to record the measured data of the valid jump.

FIG. 5 is a schematic block diagram of an apparatus 500 for vertical trajectory determination in accordance with embodiments of the present disclosure. The apparatus 500 includes wearable device 502 that can house the various hardware and software components shown in FIG. 1 and FIG. 5. The apparatus 500 includes inputs for receiving rate of turn information 101, acceleration information 102, and barometric pressure information 103. The apparatus 500 may be used in conjunction with an inertial measurement unit (IMU) providing the accelerometer and the gyroscope. In some instances, the IMU may also have a barometric altimeter integrated therewith. As used herein, the term "IMU-baro" is used to refer to such an IMU with an integrated barometric altimeter.

The rate of turn information input 101 may, for example, be connected to a gyroscope such as a tri-axial gyroscope (shown in FIG. 5 as part of MEMS-IMU 504). The acceleration information input 102 may, for example, be connected to an accelerometer such as a tri-axial accelerometer (shown in FIG. 5 as part of MEMS-IMU 304). The barometric pressure information input 103 may, for example, be connected to a barometric altimeter (shown in FIG. 5 as MEMS Barometric Altimeter 502). The apparatus 500 also includes a vertical position estimate output 104 and a vertical velocity estimate output 105.

In some embodiments of the present disclosure, the vertical position and velocity determination apparatus 500 includes a trajectory smoother 506 (shown in FIG. 5 as RTS 506). In applications where real-time data processing is not required, the accuracy of the vertical position estimate can be further improved by smoothing, which combines forward and backward processed data. In an example, the trajectory smoother of the vertical position determination apparatus 500 is configured as a Rauch-Tung-Striebel (RTS) trajectory smoother 506. The RTS smoother 506 is a widely used trajectory smoother in navigation applications, for smoothing out position and velocity trajectories.

The present disclosure provides methods and systems for vertical position and velocity determination. The vertical position and velocity determination combines vertical position information from a vertical position sensor, such as a MEMS barometric altimeter that derives altitude information using pressure measurements, with orientation (tilt angles) and acceleration information derived from a MEMS-IMU. The output of the MEMS barometric altimeter is fused with the outputs of a MEMS-IMU using a cascaded two-step Kalman filter (KF) system.

The proposed process requires a magnetometer-less MEMS-IMU to provide tilt angles and therefore, the vertical position determination is robust against magnetic disturbances. Additionally, the use of the cascaded KF avoids the need to propagate additional states, improving the computational efficiency of the position determination method. Thus, the position determination method is suitable for small and lightweight battery-powered electronic devices worn by athletes.

The present disclosure additionally provides methods and systems for automatically detecting a jump event or jump activity by an athlete. The automatic jump detection includes processing the vertical position and velocity information determined according to the various embodiments of the present disclosure.

One aspect of the present disclosure provides a vertical position and velocity determination system for inertial measurement unit (IMU) integrated with a barometric altimeter in the same device (IMU-baro). The system includes a rate of turn input connected to receive a measured IMU-baro orientation; an acceleration input connected to receive a measured IMU-baro acceleration; a barometric pressure input connected to receive a measured IMU-baro altitude; a first Kalman filter connected to the rate of turn input and to the acceleration input to estimate a roll and pitch of the IMU-baro based on the measured IMU-baro orientation and the measured IMU-baro acceleration; and a second Kalman filter connected to the acceleration input, to the barometric pressure input, and to the first Kalman filter; the second Kalman filter cascaded with the first Kalman filter to receive the estimated roll and pitch angles of the IMU-baro from the first Kalman filter and to estimate vertical position and vertical velocity of the IMU-baro based on the measured IMU-baro acceleration, the measured barometric pressure using barometric altimeter, and the estimated roll and pitch of the IMU-baro.

Another aspect of the present disclosure provides an apparatus for determining an altitude of IMU-baro. The apparatus includes a first Kalman filter configured to estimate a roll and pitch of the IMU-baro based on a measured IMU-baro rate of turn and based on a measured IMU-baro acceleration, and a second Kalman filter connected to the first Kalman filter in a cascade arrangement to receive the estimated roll and pitch of the IMU-baro. The second Kalman filter is configured to estimate a vertical position and vertical velocity of the IMU-baro based on the estimated roll and pitch of the IMU-baro, the measured IMU-baro acceleration, and a measured barometric pressure, and output the estimated vertical position and vertical velocity of the IMU-baro.

Another aspect of the present disclosure provides a method of determining vertical position and velocity of an IMU-baro. The method includes measuring a rate of turn of the IMU-baro, an acceleration of the IMU-baro, and a barometric pressure; estimating, according to a first Kalman filter operation, a roll and pitch of the IMU-baro based on the rate of turn measurement and the acceleration measurement; providing the roll and pitch estimate from the first Kalman filter operation to a second Kalman filter operation; estimating, according to the second Kalman filter operation, vertical position and velocity of the IMU-baro based on the acceleration measurement, the barometric pressure measurement, and the roll and pitch estimate; and determining the vertical position and velocity of the IMU-baro based on the estimated vertical position and velocity; and, outputting the determined vertical position and velocity.

Another aspect of the present disclosure provides a jump detection system for inertial measurement unit (IMU) integrated with a barometric altimeter in the same device (IMU-baro). The system includes a rate of turn input connected to receive a measured IMU-baro orientation; an acceleration input connected to receive a measured IMU-baro acceleration; a barometric pressure input connected to receive a measured IMU-baro altitude, a first Kalman filter connected to the rate of turn input and to the acceleration input to estimate a roll and pitch of the IMU-baro based on the measured IMU-baro orientation and the measured IMU-baro acceleration, a second Kalman filter connected to the acceleration input, to the barometric pressure input, and to the first Kalman filter, the second Kalman filter cascaded with the first Kalman filter to receive the estimated roll and pitch angles of the IMU-baro from the first Kalman filter and to estimate vertical position and vertical velocity of the IMU-baro based on the measured IMU-baro acceleration, the measured barometric pressure using barometric altimeter, and the estimated roll and pitch of the IMU-baro, and, a processor connected to the first Kalman filter and to the second Kalman filter. The processor is configured to record time-series data of both a vertical component of the measured IMU-baro acceleration and the estimated vertical velocity of the IMU-baro, detect a potential jump by comparing the vertical component of the measured IMU-baro acceleration to one or more acceleration thresholds, and, validate the potential jump by comparing a difference between a maximum velocity and a minimum velocity within a vicinity of the potential jump in the time-series data of the estimated vertical velocity of the IMU-baro to a velocity threshold.

Another aspect of the present disclosure provides a method of detecting a jump using an IMU-baro. The method includes measuring a rate of turn of the IMU-baro, an acceleration of the IMU-baro, and a barometric pressure, estimating, according to a first Kalman filter operation, a roll and pitch of the IMU-baro based on the rate of turn measurement and the acceleration measurement, providing the roll and pitch estimate from the first Kalman filter operation to a second Kalman filter operation, estimating, according to the second Kalman filter operation, vertical position and velocity of the IMU-baro based on the acceleration measurement, the barometric pressure measurement, and the roll and pitch estimate, and determining the vertical position and velocity of the IMU-baro based on the estimated vertical position and velocity, and, recording time-series data of both a vertical component of the measured IMU-baro acceleration and the estimated vertical velocity of the IMU-baro, detecting a potential jump by comparing the vertical component of the measured IMU-baro acceleration to one or more acceleration thresholds. And validating the potential jump by comparing a difference between a maximum velocity and a minimum velocity within a vicinity of the potential jump in the time-series data of the estimated vertical velocity of the IMU-baro to a velocity threshold.

In the preceding description, for purposes of explanation, numerous details are set forth in order to provide a thorough understanding of the embodiments. However, it will be apparent to one skilled in the art that these specific details are not required. In other instances, well-known electrical structures and circuits are shown in block diagram form in order not to obscure the understanding. For example, specific details are not provided as to whether the embodiments described herein are implemented as a software routine, hardware circuit, firmware, or a combination thereof.

Embodiments of the disclosure can be represented as a computer program product stored in a machine-readable medium (also referred to as a computer-readable medium, a processor-readable medium, or a computer usable medium having a computer-readable program code embodied therein). The machine-readable medium can be any suitable tangible, non-transitory medium, including magnetic, optical, or electrical storage medium including a diskette, compact disk read only memory (CD-ROM), memory device (volatile or non-volatile), or similar storage mechanism. The machine-readable medium can contain various sets of instructions, code sequences, configuration information, or other data, which, when executed, cause a processor to perform steps in a method according to an embodiment of the disclosure. Those of ordinary skill in the art will appreciate that other instructions and operations necessary to implement the described implementations can also be stored on the machine-readable medium. The instructions stored on the machine-readable medium can be executed by a processor or other suitable processing device, and can interface with circuitry to perform the described tasks.

The above-described embodiments are intended to be examples only. Alterations, modifications and variations can be effected to the particular embodiments by those of skill in the art. The scope of the claims should not be limited by the particular embodiments set forth herein, but should be construed in a manner consistent with the specification as a whole.

The invention claimed is:

1. A jump detection system for a device comprising an inertial measurement unit (IMU) integrated with a barometric altimeter in the same device, the jump detection system comprising:
   a first Kalman filter connected to a rate of turn input and to an acceleration input to estimate a roll and pitch of the device based on the rate of turn input and the acceleration input;
   a second Kalman filter connected to the acceleration input, to a barometric pressure input, and to the first Kalman filter; the second Kalman filter cascaded with the first Kalman filter to receive the estimate of the roll and pitch of the device from the first Kalman filter and to estimate vertical position and vertical velocity of the device based on the acceleration input, the barometric pressure input using barometric altimeter, and the estimate of the roll and pitch of the device; and
   a processor connected to the first Kalman filter and to the second Kalman filter, the processor configured to:
      record time-series data of both a vertical component of the acceleration input and the estimate of the vertical velocity of the device;
      detect a potential jump by comparing the vertical component of the acceleration input to one or more acceleration thresholds; and
      validate the potential jump by comparing a difference between a maximum velocity and a minimum velocity within a threshold range of the potential jump in the time-series data of the estimate of the vertical velocity of the device to a velocity threshold.

2. The jump detection system of claim 1, wherein the processor is further configured to detect a potential jump takeoff by comparing the vertical component of the acceleration input to a first acceleration threshold and detect a potential jump landing by comparing the vertical component of the acceleration input to a second acceleration threshold.

3. The jump detection system of claim 2, wherein the processor is further configured to record a duration of the potential jump based on the detection of the potential jump and detection of the potential jump landing, and to compare the duration of the potential jump to a duration threshold in order to further validate the potential jump.

4. The jump detection system of claim 3, wherein the processor determines the difference in the time-series data of the estimate of the vertical velocity by searching for a maximum vertical velocity at a time before a start of the potential jump and searching for a minimum vertical velocity at a time after an end of the potential jump, and by subtracting the minimum vertical velocity from the maximum vertical velocity.

5. The jump detection system of claim 1, wherein the processor is further configured to record characteristics of the validation of the potential jump.

6. A computer program product, comprising a non-transitory computer readable storage medium having a computer readable program code embodied therein, the computer readable program code adapted to be executed to implement instructions to:
   measure a rate of turn of an IMU-baro, an acceleration of the IMU-baro, and a barometric pressure;
   estimate, according to a first Kalman filter operation, a roll and pitch of the IMU-baro based on the rate of turn and the acceleration;
   provide the roll and pitch estimate from the first Kalman filter operation to a second Kalman filter operation;
   estimate, according to the second Kalman filter operation, a vertical position and a vertical velocity of the IMU-baro based on the acceleration, the barometric pressure, and the roll and pitch estimate;

determine the vertical position and the vertical velocity of the IMU-baro based on the estimate of the vertical position and the vertical velocity;

record time-series data of both a vertical component of the acceleration and the estimate of the vertical velocity of the IMU-baro;

detect a potential jump by comparing the vertical component of the acceleration to one or more acceleration thresholds; and validate the potential jump by comparing a difference between a maximum velocity and a minimum velocity within a threshold range of the potential jump in the time-series data of the estimate of the vertical velocity of the IMU-baro to a velocity threshold.

7. The computer program product of claim 6, the computer readable program code further adapted to be executed to implement instructions to detect a potential jump takeoff by comparing the vertical component of the acceleration to a first acceleration threshold and detect a potential jump landing by comparing the vertical component of the acceleration to a second acceleration threshold.

8. The computer program product of claim 6, the computer readable program code further adapted to be executed to implement instructions to record a duration of the potential jump based on the detection of the potential jump and detection of the potential jump landing, and to compare the duration of the potential jump to a duration threshold in order to further validate the potential jump.

9. The computer program product of claim 6, the computer readable program code further adapted to be executed to implement instructions to determine the difference in the time-series data of the estimate of the vertical velocity by searching for a maximum vertical velocity at a time before a start of the potential jump and identify for a minimum vertical velocity at a time after an end of the potential jump, and by subtracting the minimum vertical velocity from the maximum vertical velocity.

10. The computer program product of claim 6, further comprising recording characteristics of the validation of the potential jump.

11. An apparatus for jump detection including an inertial measurement unit (IMU) integrated with a barometric altimeter in the same apparatus, the apparatus comprising:

a first Kalman filter connected to a rate of turn input and to an acceleration input to estimate a roll and pitch of the apparatus based on the rate of turn input and the acceleration input;

a second Kalman filter connected to the acceleration input, to a barometric pressure input, and to the first Kalman filter; the second Kalman filter cascaded with the first Kalman filter to receive the estimate of the roll and pitch of the apparatus from the first Kalman filter and to estimate a vertical position and a vertical velocity of the apparatus based on the acceleration input, the barometric pressure input using barometric altimeter, and the estimate of the roll and pitch of the apparatus; and a processor connected to the first Kalman filter and to the second Kalman filter, the processor configured to:

record time-series data of both a vertical component of the acceleration input and the estimate of the vertical velocity of the apparatus;

detect a potential jump by comparing the vertical component of the acceleration input to one or more acceleration thresholds; and validate the potential jump by comparing a difference between a maximum velocity and a minimum velocity within a threshold range of the potential jump in the time-series data of the estimate of the vertical velocity of the apparatus to a velocity threshold.

12. The apparatus of claim 11, wherein the processor is further configured to detect a potential jump takeoff by comparing the vertical component of the acceleration input to a first acceleration threshold and detect a potential jump landing by comparing the vertical component of the acceleration input to a second acceleration threshold.

13. The apparatus of claim 12, wherein the processor is further configured to record a duration of the potential jump based on the detection of the potential jump and detection of the potential jump landing, and to compare the duration of the potential jump to a duration threshold in order to further validate the potential jump.

14. The apparatus of claim 13, wherein the processor determines the difference in the time-series data of the estimate of the vertical velocity by searching for a maximum vertical velocity at a time before a start of the potential jump and searching for a minimum vertical velocity at a time after an end of the potential jump, and by subtracting the minimum vertical velocity from the maximum vertical velocity.

15. The apparatus of claim 11, wherein the processor is further configured to record characteristics of the validation of the potential jump.

\* \* \* \* \*